(12) United States Patent
Kligman et al.

(10) Patent No.: US 6,869,611 B1
(45) Date of Patent: Mar. 22, 2005

(54) COMPOSITION AND METHOD OF EFFECTING SUPERFICIAL CHEMICAL SKIN PEELS

(76) Inventors: Douglas E. Kligman, 151 E. Tenth St., Conshohocken, PA (US) 19428; Albert M. Kligman, 151 E. Tenth St., Conshohocken, PA (US) 19428

( * ) Notice: Subject to any disclaimer, the term of this patent is extended or adjusted under 35 U.S.C. 154(b) by 0 days.

(21) Appl. No.: 09/131,076

(22) Filed: Aug. 7, 1998

Related U.S. Application Data

(63) Continuation of application No. PCT/US97/01919, filed on Feb. 5, 1997, and a continuation-in-part of application No. 08/597,370, filed on Feb. 8, 1996, now abandoned.

(51) Int. Cl.[7] .......................... A61K 7/00; A61K 7/42; A61K 7/44
(52) U.S. Cl. .......................... 424/401; 424/59; 424/60
(58) Field of Search ........................... 424/59, 60, 401; 514/887

(56) References Cited

U.S. PATENT DOCUMENTS

| | | | |
|---|---|---|---|
| 2,942,008 A | | 6/1960 | Lubowe |
| 3,236,730 A | | 2/1966 | Galin |
| 3,265,571 A | | 8/1966 | Krezanoski |
| 4,318,907 A | * | 3/1982 | Kligman et al. .......... 424/230 |
| 4,381,296 A | | 4/1983 | Tinnell |
| 4,514,385 A | * | 4/1985 | Damani et al. ............ 424/81 |
| 4,588,590 A | | 5/1986 | Bernstein ................ 424/195 |
| 4,608,370 A | | 8/1986 | Aronsohn |
| 4,800,197 A | | 1/1989 | Kowcz et al. |
| 4,954,487 A | | 9/1990 | Cooper et al. |
| 5,167,649 A | | 12/1992 | Zook |
| 5,296,476 A | | 3/1994 | Henderson |
| 5,382,432 A | * | 1/1995 | McCook et al. .......... 424/401 |
| 5,449,519 A | | 9/1995 | Wolf et al. |
| 5,573,759 A | | 11/1996 | Blank |
| 5,595,984 A | | 1/1997 | Blank |
| 5,597,813 A | | 1/1997 | Blank |
| 5,597,814 A | | 1/1997 | Blank |
| 5,604,212 A | | 2/1997 | Blank |
| 5,605,894 A | | 2/1997 | Blank et al. |
| 5,723,109 A | * | 3/1998 | Causse et al. ............. 424/62 |
| 5,730,991 A | * | 3/1998 | Rapaport ................. 424/401 |
| 5,741,497 A | * | 4/1998 | Guerrero et al. .......... 424/401 |
| 5,811,101 A | * | 9/1998 | Waltman ................ 424/195.1 |
| 5,948,416 A | * | 9/1999 | Wagner et al. ............ 424/401 |

FOREIGN PATENT DOCUMENTS

| | | |
|---|---|---|
| DE | 29 45 979 A1 | 5/1981 |
| EP | 0 327 326 A1 | 8/1989 |
| WO | WO 93/10756 * | 6/1993 |

OTHER PUBLICATIONS

Rubin, Mark G., *Manual of Chemical Peels: Superficial and Medium Depth*, "Chapter 2: What Are Skin Peels?," pp. 17–25 (1995).
Rubin, Mark G., *Manual of Chemical Peels: Superficial and Medium Depth*, "Chapter 7: Glycolic Acid Peels," pp. 89–102 (1995).
Kligman, Douglas, E., et al., "Salicylic Acid Peels for the Treatment of Photoaging," *Dermatological Surgery*, 24: 325–328 (1998).
Kligman, Douglas et al., "Salicylic Acid as a Peeling Agent for the Treatment of Acne,"*Cosmetic Dermatology*, 10: 44–47 (Sep. 1997).
Grimes, Pearl E., "The Safety and Efficacy of Salicylic Acid Chemical Peels in Darker Racial–Ethnic Groups," *Dermatological Surgery*, 25: 18–22 (1999).
Imayama, Shuhei, et al., "Histologic Changes in the Skin of Hairless Mice Following Peeling With Salicylic Acid," *Archives of Dermatology*, 136: 1390–1395 (Nov. 2000).
Mark G. Rubin, *Manual of Chemical Peels –Superficial and Medium Depth*, pp. 79–88, 103–109 & 170–176, J.B. Lippincott Company, Philadelphia, PA (1995);
Robert B. King, "Topical Aspirin in Chloroform and the Relief of Pain due to Herpes Zoster and Postherpetic Neuralgia," *Arch Neurol.* 50, pp. 1046–1053 (Oct. 1993).
Harold J. Brody, *Chemical Peeling*, pp. 53–73, Mosby Year Book, Inc., St. Louis, MO (1992).
James M. Swinehart, "Salicylic Acid Ointment Peeling of the Hands and Forearms," *J. Dermatol. Surg. Oncol.*, 18, pp. 495–498 (1992).
Harold J. Brody, "Variations and Comparisons in Medium–Depth Chemical Peeling," *J. Dermatol. Surg. Oncol.*, 15:9, pp. 953–963 (Sep. 1989).
Abstract 8301 –Salicylic Acid, *The Merck Index*, p. 1324, Merck & Co., Inc., Rahway, NG (1989).
Abstract 84956p, *Chemical Abstracts*, 105, p. 394(1989).
Abstract 11490f, *Chemical Abstracts*, 103, p. 340 (1985).
Abstract 119635a, *Chemical Abstracts*, 102, p. 401 (1985); and.
Abstract 67481z, *Chemical Abstracts*, 75, p. 238 (1971).

* cited by examiner

*Primary Examiner*—Gollamudi S. Kishore
*Assistant Examiner*—S. Tran
(74) *Attorney, Agent, or Firm*—Akin Gump Strauss Hauer & Feld LLP

(57) ABSTRACT

A method for effecting a superficial chemical skin peel is provided wherein a concentrated solution of salicylic acid in a dermatologically acceptable solvent is applied to be treated. The concentrated salicylic acid solution contains at least 15 wt % salicylic acid and preferably at least about 20 wt % salicylic acid, The composition and method are useful in the treatment of skin disorders such as photodamaged skin, hyperpigmentation, acne vulgaris, and the like.

12 Claims, No Drawings

COMPOSITION AND METHOD OF EFFECTING SUPERFICIAL CHEMICAL SKIN PEELS

CROSS-REFERENCE TO RELATED APPLICATIONS

This application is a continuation of International Application PCT/US97/01919, filed Feb. 5, 1997 (WO 97/28786), which is in turn a continuation-in-part of U.S. Application Ser. No. 08/597,370, filed Feb. 8, 1996, now abandoned.

BACKGROUND OF THE INVENTION

This invention relates to a composition and method for effecting superficial chemical skin peels, particularly, utilizing compositions containing salicylic acid.

Skin peeling techniques have long been used for therapeutic benefit to treat a wide spectrum of skin disorders deemed as being aesthetically or medically undesirable. Such skin disorders most commonly affect facial skin and include photodamaged skin, typically resulting from exposure to sunlight or other ultraviolet sources; hyperpigmentation, including melasma, mottled spots, "liver" or "age" spots, freckles; wrinkled, rough or "weathered" skin; and premalignant neoplasms (also called premalignant skin cancer) such as actinic keratoses.

Conventional skin peeling procedures include mechanical removal, e.g., dermabrasion or $CO_2$ laser, and chemical-induced skin removal. Chemical skin peeling techniques are currently very popular for treating the skin disorders described above and are often categorized by the degree or amount of skin removal effected.

Chemical peels may be categorized as superficial, medium and deep chemical peels, depending on the depth of chemical wounding of the skin that occurs. Superficial chemical peels are those which remove or effect accelerated replacement or replenishment of the epidermis. Popular superficial chemical peeling agents include α-hydroxy acids, e.g., glycolic acid or other "fruit acids" such as citric and lactic acids; trichloroacetic acid; resorcinol and Jessner's solution. Medium depth peels penetrate to the papillary dermis and typically use 40–50% trichloroacetic acid as the chemical peeling agent. Deep peels penetrate to the reticular dermis and typically use phenol as the chemical peeling agent. Superficial chemical peels are most commonly used in treating skin disorders such as described above, particularly photodamaged skin, and glycolic acid is the most popular chemical peeling agent for such peels.

Jessner's solution, mentioned above, has been used in superficial chemical skin peeling to treat photodamaged skin and other facial skin disorders. Salicylic acid is one component utilized in Jessner's solution, an ethanol solution containing equal parts (about 14%) of resorcinol, salicylic acid and lactic acid (85%); see Brody, *Chemical Peeling*, Mosby Year Book, St. Louis, Mo., pp. 59–60 (1992) and Rubin, *Manual of Chemical Peels*, J. B. Lippincott Company, Philadelphia, Penn., pp. 79–88 (1995).

Salicylic acid is a well-known compound that is recognized for its usefulness as a "keratolytic" agent and as a precursor in the manufacture of salicylate derivatives, such as analgesics. Salicylic acid is a powder that is relatively insoluble in water and has been used at low concentrations in alcoholic solutions or in other carriers or, in solid form, as a plaster, paste or ointment composition.

U.S. Pat. No. 5,449,519 of Wolfe et al. describes cosmetic compositions with keratolytic and anti-acne activity, that contain a keratolytic compound, ie., salicylic acid, resorcinol and/or benzoyl peroxide, complexed to an amino- or hydroxy-containing carrier such as a protein. The compositions contain 0.1–30% keratolytic compound complex and 70–99.9% diluent, such as a cream, lotion, toner, or other cosmetically acceptable diluent.

Salicylic acid, benzoyl peroxide and resorcinol have long been utilized for acne treatment in aqueous ethanol solutions at low concentrations, e.g., less than about 10% salicylic acid (typically 1–7% salicylic acid) and less than about 20% benzoyl peroxide (typically 3–10% benzoyl peroxide). U.S. Pat. No 4,318,907 of Kligman et al. discloses such compositions but cautions against using higher concentrations of salicylic acid, noting (column 2, lines 49–52) that 10% salicylic acid with 5% benzoyl peroxide caused excessive redness and peeling in many patients treated.

Salicylic acid has been used in solid form for the treatment of warts, as a plaster containing 40% salicylic acid that is applied with adhesive tape to the wart for several days. Salicylic acid has also been utilized in chemical peels for treatment of photodamaged skin on the hands and forearms, in the form of a salicylic acid paste or ointment. Such treatments typically involve application of a thick coating of ointment, containing 50% salicylic acid, to the affected skin, then wrapping the treated areas with Saran Wrap® plastic wrap secured with tape, followed by a 48 hours occlusion period after which the dressing is removed; see Swinehart, "Salicylic Ointment Peeling of the Hands and Forearms",*J. Dermatol Surg. Oncol.* 18, pp. 495–498 (1992). The inconvenience of this treatment is unacceptable for many patients, and Swinehart does not suggest that this technique might be usefull for treatment of facial skin. Besides the inconvenience to the patient during treatment, this procedure is also subject to a risk of salicylism, i.e., toxic effects from systemic absorption of salicylic acid during the prolonged treatment period. The use of a salicylic acid paste or ointment as described by Swinehart, supra, for treating damaged skin on the hands and forearms is also mentioned by Brody, op. cit., at pages 60–63 and by Rubin, op. cit., at pages 103–109.

U.S. Pat. No. 4,954,487 of Cooper et al. describes topically administered pharmaceutical compositions with a two-component skin penetration enhancer for delivering a pharmaceutical active across intact skin. The compositions may contain antibiotics, local anesthetics, benzoyl peroxide or non-steroidal anti-inflammatory drugs (NSAIDs), including salicylic acid, at a concentration of 0.01–35 wt % in 0–70% ethanol with 5–99% skin penetration enhancer. The antibiotic containing or benzoyl peroxide-containing compositions are described as useful for the treatment of acne, but the NSAID-containing compositions are described only as useful for treating and preventing pain and inflammation in humans and lower animals.

A need exists for a superficial chemical skin peeling technique that provides exceptional improvement for skin disorders such as described earlier, without the adverse side effects or drawbacks of conventional superficial chemical peels.

SUMMARY OF THE INVENTION

The present invention is a method for effecting a superficial chemical skin peel by topically applying to skin to be treated a composition comprising a solution of salicylic acid containing at least 15 wt % salicylic acid, based on the weight of the solution, in a dermatologically acceptable liquid solvent. In this method, the applied salicylic acid solution is preferably allowed to dry on the treated skin, and the treated skin is then wiped or washed to remove any residue from the applied solution.

The composition and method of this invention are useful in the treatment of skin disorders, particularly those affecting facial skin, such as photodamaged skin, hyperpigrnentation, acne vulgaris, rosacea, premalignant skin cancer, wrinkles, superficial scars and the like.

Another aspect of the invention is a composition useful for superficial chemical skin peels consisting essentially of a solution of salicylic acid dissolved in a dermatologically acceptable liquid solvent, the amount of salicylic acid being at least 15 wt %, based on the weight of the solution, said solution also containing at least one dermatologically acceptable adjuvant in an amount of from about 0.01 to about 5 wt %, based on the weight of the solution.

The salicylic acid solutions of the composition and method of this invention preferably contain salicylic acid in an amount of at least about 20 wt %, more preferably about 25 wt %, based on the weight of the solution. Ethanol is a preferred solvent.

Yet another aspect of the invention is a composition useful for the treatment of skin disorders that consists essentially of salicylic acid dissolved in aqueous ethanol, in an amount of at least 15 wt % based on the weight of the solution, the aqueous ethanol containing about 85 to 99 wt % ethanol.

DETAILED DESCRIPTION OF THE PREFERRED EMBODIMENTS

Salicylic acid, also known as 2-hydroxybenzoic acid or orthohydroxybenzoic acid, has the formula:

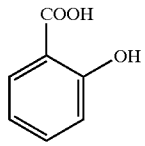

Salicylic acid is a well-known chemical (see, e.g., *Merck Index*, 11th Edition, Budavari et al., eds., Merck & Co., Rahway, N.J. (1989), Listing No. 8301, p. 1324) that is readily available in highly purified form, more than 99% pure, from a variety of commercial sources, including chemical and laboratory supply houses. Methods for manufacturing salicylic acid are also well known and reported in the literature. Cosmetic grade and United States Pharmacopoeia grade salicylic acid are preferred for use in this invention.

Salicylic acid per se is preferred for use in this invention. The inventors believe, however, that derivatives of salicylic acid, e.g., esters, salts and other dermatologically effective derivatives of salicylic acid, may also exhibit similar functionality when used as concentrated solutions in lieu of the preferred salicylic acid in this invention, and such functional equivalents of salicylic acid are intended to be within the scope of the present invention.

In the present invention, the salicylic acid must be dissolved in the derrnatologically acceptable solvent in large amounts to provide a highly concentrated solution of salicylic acid. The concentration of salicylic acid in the dermatologically acceptable solvent in this invention is at least 15 wt %. Below a concentration of 15 wt %, the salicylic acid does not provide the desired efficacy provided by concentrated salicylic acid solutions, i.e., containing at least 15 wt %, preferably at least 20 wt % salicylic acid. More preferably, the salicylic acid concentration in the solution is at least about 25 wt % and most preferably is at least about 30 wt %. All weight percentages in this specification referring to the concentration of salicylic acid or other components in solution are based on the total weight of the solution.

The upper limit of the concentration of salicylic acid dissolved in the solvent is ordinarily limited to its saturation concentration in the solvent The saturation concentration for salicylic acid in a solvent will ordinarily vary with temperature, being higher as the solution temperature is increased. In ethanol, a preferred solvent, the saturation concentration of salicylic acid is in excess of 30 wt %, at a solution temperature of 25° C. The upper limit of salicylic acid dissolved in the solvent is preferably limited to 40 wt % salicylic acid, for those solvents in which the saturation concentration of salicylic acid is greater than 40 wt %.

The solvent employed for the concentrated salicylic acid solution of this invention is a dermatologically acceptable liquid solvent in which salicylic acid is soluble at high concentrations. The term "dermatologically acceptable" solvent is intended to mean those solvents which can safely be used on the skin in the topical treatment method of this invention, i.e., solvents which do not provoke a severe reaction and which are not toxic when contacted with the skin for relatively short periods of time. Preferred solvents are organic solvents that are relatively volatile, to facilitate evaporation of the solvent after application of a coating of the salicylic acid-containing solution onto the skin. Volatile solvents with moderate flash points, e.g., above 30° C., are preferred for safety reasons, to minimize flammability risks.

Preferred solvents are ethanol and isopropanol. Other suitable solvents include methanol, acetone, ether (diethyl ether) and propylene glycol. Mixtures containing one or more of these solvents or other solvents may also be used.

Ethanol is the most preferred solvent. The ethanol may also be aqueous ethanol, preferably containing about 85 to 99 wt % ethanol and more preferably containing about 90 to 95 wt % ethanol. The ethanol employed as the solvent is preferably a grade of ethanol suitable for use in cosmetics or in pharmaceutical formulations.

Other solvents or solvent mixtures, including solvents less volatile than the preferred ethanol and isopropanol and including polymeric solvents, may also be employed provided that the minimum salicylic acid can be solubilized therein at high concentrations.

As indicated above for ethanol, the preferred organic solvents may also contain some water, if miscible with the solvent. The aqueous fraction of the solvent mixture is desirably minimized since its presence typically reduces the saturation concentration of salicylic acid in the solvent, as the proportion of water is increased. The concentration of water in the non-aqueous solvent is preferably not more than about 15 wt %, and more preferably not more than about 10 wt %, and most preferably not more than about 5 wt %.

The concentrated salicylic acid solution may be prepared by introducing solid salicylic acid, in crystalline or powdered form, into the solvent with mixing. The salicylic acid and solvent may be provided in such relative amounts that provide the desired concentration, e.g., 30 wt %. Altenatively, an excess of salicylic acid may be provided and mixed with the solvent so as to provide a saturated salicylic acid solution. Dissolution of the salicylic acid may be promoted by mild heating of the solvent, with proper precautions being taken with those solvents that have a very low flash point, i.e., solvents that are highly flammable.

The concentrated salicylic acid solution may contain minor amounts of other components that are not essential to the present invention, such as preservatives, stabilizers, antioxidants, thickening agents, surfactants, pigments, colorants, fragrances and other adjuvants. Such dermatologically acceptable adjuvants may be present individually or in combination. The concentration of dermatologically acceptable adjuvant may be from about 0.01 to about 5 wt %, based on the weight of the concentrated salicylic acid solution. Preferably, the amounts of such adjuvants are minimized so as not to cause a significant reduction in the maximum, i.e., saturation, concentration of salicylic acid in the solvent.

The concentrated salicylic acid solution is preferably applied to the skin to be treated at a solution temperature of about 15° C. to about 30° C., about 20° C. to about 25° C. being preferred. For solvents other than the preferred ethanol, the solvent volatility characteristics may dictate use of the solution at a temperature outside of these ranges, e.g., use of lower temperatures for highly volatile solvents.

The skin to be treated according to this invention is desirably first cleaned with ethanol, but this step is optional and not essential to the teatrnent method of this invention. The cleaning may be accomplished by gently wiping the skin with a gauze square wetted with ethanol or acetone, immediately before the treatment with concentrated salicylic acid solution is begun. This cleaning is intended to degrease the skin and to remove makeup and debris, as well as sebum. Other cleaning or degreasing agents may also be used but are less preferred than ethanol. While unnecessary to the present invention, other conventional skin preparation techniques may also be used in advance of the skin treatment according to this invention.

The concentrated salicylic acid solution is topically applied to the skin to be treated. This is typically accomplished with an absorbent cotton swab wetted with the concentrated solution, with a solution-wetted sable brush or by gentle wiping with a solution-wetted absorbent fibrous material such as a gauze square or nonwoven pad, but other solution application techniques that uniformly coat the skin with the solution are also feasible.

The applied solution is normally allowed to air dry over a relatively short period of time, preferably being less than 15 minutes and, with the preferred ethanol solvent, typically being in the range of about 3 to 10 minutes. With solvents that may be less volatile than the preferred ethanol solvent, such drying may be promoted by directing a gentle stream of air, preferably warm air, onto the treated area or by other analogous procedures. A single uniform application of the concentrated salicylic acid solution on the skin to be treated is generally sufficient for treatment of facial skin disorders. Additional or multiple applications either before or immediately after the applied solution has dried are normally unnecessary but may be usefuil in some situations, e.g., in treating skin on other parts of the body or in treating severely photodamaged skin.

It should be understood that once the applied solution has dried on the treated skin, the treatment method of this invention is essentially complete. With salicylic acid solutions using a preferred volatile solvent, drying of the applied solution on the treated skin occurs relatively quickly in a few minutes.

Once the concentrated solution has dried on the treated skin, the skin is thereafter preferably wiped or washed, to remove any residue or traces of the applied concentrated salicylic acid solution, including any deposits of salicylic acid that may remain after drying. This step, however, is not critical but is merely preferred.

In situations where a relatively nonvolatile solvent is employed and the concentrated solution does not quickly dry on the treated skin, the skin is preferably wiped or washed no later than about one hour, and preferably no more than about 15 minutes, after application of the concentrated salicylic acid solution, to remove all traces of the applied solution. This period, of no more than about one hour, and preferably no more than about 15 minutes, is normally more than sufficient to provide the desired benefits resulting from treatment according to this invention.

Preferably, the treated skin is washed or wiped with water, e.g., with a water-moistened or water-wet swab, gauze square, or the like. Other solutions, such as an aqueous solution of mild detergent, aqueous alcohol solutions or isopropanol or ethanol, and the like, may also be used for this purpose. After the treated skin is wiped or washed as just described, the treatment according to this invention is essentially complete, with no further steps being required. Additional applications of the concentrated salicylic acid solution immediately after the wiping/washing step, followed by drying and repeated wiping/washing, are generally unnecessary for treating facial skin disorders but, as noted above, may be desirable in some circumstances.

During the period generally beginning a few days, e.g., about 2 to 5 days, after the treatment with the concentrated salicylic acid solution, a typical patient will experience some peeling and scaling of the treated skin. The peeling and scaling will generally last no more than about 7 days and may be as short as 2 or 3 days in duration. Although the present invention does not require any special steps to be taken during this period, a bland or mild moisturizer may be applied, as desired, to the treated skin to reduce the visibility of scaling, peeling skin and to reduce skin dryness. Following the peeling period, the skin treated in the method of this invention may be treated further, with conventional skin treatment therapies, but such therapies are not a part of this invention.

The concentrated salicylic acid solution of this invention is useful for treating a variety of skin disorders, particularly those affecting facial skin, and is particularly useful in superficial facial skin peels. Skin disorders that may be treated include photodamaged skin; hyperpigmentation, including melasma; acne vulgaris, including inflammatory acne, comedonal acne and mild-to-moderate scarring resulting from acne; rosacea; premalignant skin cancer; wrinkling and superficial scarring; and the like.

Photodamaged skin typically results from ultraviolet light exposure from sunlight. Skin changes that result may include roughness; wrinkling; hyperpigmentation, e.g., freckles, age or "liver" spots, melasma or mottled pigmentation; and loss of elasticity. While the method of this invention is especially useful for treating photodamaged facial skin, it is also useful for treating skin on other sun-exposed areas of the body, such as forearms, backs of hands, lower legs and upper torso, including the neck.

Patients with melasma, a type of hyperpigmentation resulting from excessive localized production of melanin which creates patches of hyperpigmentation, also benefit from treatment according to this invention. The treatment leads to bleaching out of the hyperpigmentation, resulting in a more uniform coloration.

In view of the outstanding benefits provided by the concentrated salicylic acid solution of this invention, the inventors believe that analogous skin disorders in animals, i.e., other than humans, may also be susceptible to treatment according to this invention.

The treatment method of this invention provides numerous unexpected advantages and benefits including those described below, not associated with other, prior art techniques for effecting superficial chemical peels.

The method involves minimal discomfort to the patient, since a typical patient experiences stinging or burning for only a short period, e.g., a few minutes, after the concentrated salicylic acid solution is applied to the skin. A typical patient finds that the stinging, burning sensation ceases soon after the concentrated salicylic acid solution is applied to the skin, even before the treated skin is subsequently wiped to remove any residue. This contrasts with conventional superficial skin peeling techniques, e.g., using glycolic acid, which cause stinging and burning that increase during the time the chemical agent is in contact with the skin.

The treatment with concentrated salicylic acid appears to effect a mild or partial anesthesia of the treated skin. The treated skin is anesthetized to touch and mild pain (but not to pain such as a needle prick).

Unlike some traditional chemical peel techniques which cause a patient to withdraw from normal work and social activities, the typical patient is able to return to normal activities immediately following treatment according to this invention. Taking into account the remarkable benefits and improvements provided by this invention in treating skin disorders, one cannot easily overstate the significant advantage of the present technique in avoiding patient "downtime" and discomfort The method of this invention is also characterized by its relative absence of pigmentary complications, such as hypopigmentation and hyperpigmentation. The treatment method is consequently very useful for treating skin disorders in Asian or oriental patients and in darker skinned or black patients.

Another finding with this invention is the virtual absence of bacterial infections or viral infections of the treated skin. The risk of scarring is also minimal.

While not wishing to be bound by a particular theory or mechanism, the inventors believe that the treatment method of this invention functions in a different manner from traditional chemical peels.

Unlike some traditional chemical peeling techniques, e.g., trichloroacetic acid skin peels, which result in necrosis of the viable epidermis, the concentrated salicylic acid solution of this invention is believed to effect its beneficial results, including its keratolytic activity, with the viable epidermis remaining essentially intact.

Yet another advantage of the method of this invention is that the treatment time, i.e., the period during which the treated skin is exposed to the salicylic acid in the concentrated solution, is normally self-limiting and is not dependent on the intervention of the applicator for determining length of treatment time or determining when the treatment period should terminate. For volatile solvents such as the preferred ethanol solvent, the evaporation of the solvent from the coating of concentrated salicylic acid solution is effective for controlling the treatment time, ensuring not only constancy in treatment time, but also avoiding the need for applicator intervention to avoid excessively long exposure to the solution of concentrated salicylic acid.

A related benefit is the ease of ensuring that a uniform application of concentrated salicylic acid is made on the area of skin to be treated. When the volatile solvent evaporates, the treated skin presents the appearance of having a white frosting from the residual salicylic acid that is precipitated from the applied concentrated solution. Areas of skin to be treated which have been missed during application of the concentrated salicylic acid are easily discerned, and inadvertent second applications of the concentrated salicylic acid solution can also be readily avoided. The superficial anesthetia provided by the concentrated salicylic acid also aids in the treatment procedure and promotes patient cooperation, by minimizing patient discomfort during the procedure.

While the inventors do not intend to limit the scope of their invention by any theory of operation, they believe that the following explanation may assist in understanding the present invention. The inventors believe that the treatment with a concentrated salicylic acid solution effects the following changes:

absence of skin necrosis: only the stratum corneum is sloughed off, and the underlying epidermis is not destroyed or killed;

exfoliation of skin cells, from the stratum corneum, stimulating faster proliferation of cells in the stratum granulosum;

increased proliferation of the epidermis that retards accumulation of melanin granules in the epidermis;

replacement of photodamaged skin with new "normnal" skin, lacking the abnormalities of the photodamaged skin, as evidenced by correction of atypia and atrophy.

With a volatile solvent such as ethanol, the concentrated salicylic acid solution applied to the skin to be treated dries or is dried quickly by evaporation of the solvent, leaving a deposit of salicylic acid on the surface of the skin. The efficacy and benefits provided by the concentrated salicylic acid solution appear due to its residence time as a solution on the surface of the skin, not as a dry residue after evaporation of the solvent. Thus, treatment time according to this invention should be measured as the time of exposure of the treated skin to the concentrated solution, with treatment time ending once the volatile solvent has evaporated from the applied solution or once the still-wet coating of applied concentrated solution is wiped or otherwise removed from the skin.

The efficacy and benefits of the concentrated salicylic acid solution of this invention also appear due to its presence substantially on the surface of the skin.

In contrast, some prior art applications of nonsteroidal anti-inflammatory drugs have employed a skin penetration enhancer to facilitate transdermal administration of the drug into the body. Such penetration enhancers are not only unnecessary in the present invention, but also undesirable, since absorption of salicylic acid in significant concentrations into the circulatory system can result in salicylate-caused systemic poisoning, i.e, salicylism. Use of the concentrated salicylic acid solution in the method of the present invention, in which skin or transdermal penetration enhancers are substantially or essentially absent, does not appear to result in any significant absorption of salicylic acid into the patient being treated, and the likelihood of a typical patient experiencing salicylism is remote.

The invention is further illustrated by the following nonlimiting Example.

PROTOCOL

A solution containing about 30–31% by weight salicylic acid dissolved in ethanol was utilized in this example and was prepared by introducing 35 parts by weight salicylic acid into 100 parts by volume of 95 wt % ethyl alcohol (containing 5 wt % water), with mixing, to form a concentrated salicylic acid solution.

The facial skin of a patient to be treated in the superficial chemical skin peeling method of this invention was first cleaned with ethanol, to degrease the skin and to remove makeup and debris, as well as skin oil. This was accomplished by gently wiping the facial skin with a gauze square wetted with ethanol, immediately before the treatment with concentrated salicylic acid solution was begun.

Following the cleaning step, which is optional but preferred, the facial skin was then treated with the concentrated salicylic acid solution. The concentrated salicylic acid solution was topically applied in a single, uniform coating by swabbing with solution-wetted cotton swabs to the entire area being treated, at ambient temperature, about 20–25° C. The salicylic acid solution was allowed to air dry on the treated skin over a period of about three to five minutes.

A typical patient experienced some stinging and burning sensation in the treated area after about one minute. This sensation typically reached a peak at about three minutes after the salicylic acid solution was first applied, and this was soon followed by superficial anesthesia in which the stinging and burning sensation subsided.

After the salicylic acid solution had air dried, the treated facial skin was then washed with water, by the patient's hand washing the treated areas at a sink.

In a typical patient, minimal scaling or peeling of the treated skin was evident until about 2 to about 5 days after the treatment. Scaling and peeling of the treated skin typically extended for up to about 7 days. Erythema and edema were minimal in a typical patient during the scaling/peeling period. A bland, fragrance-free moisturizer was applied, once scaling or peeling began, and application of the moisturizer was continued until peeling ceased. In contrast to many prior art peeling techniques, the typical patient was able to resume normal work and social activity immediately, and there was no need to withdraw from such activity during the peeling period.

Once scaling and peeling had substantially ended, the improvement to the treated skin was clearly evident. In patients with acne vulgaris, treatment with the concentrated salicylic acid solution according to this invention rapidly brought this skin disorder under control, by providing rapid extrusion of comedones, both blackheads and whiteheads, in comedonal acne, and by providing resorption of pustules in inflammatory acne. In patients with acne-caused shallow scaring, the treatment was also beneficial for improving the appearance of skin, by providing skin with a smoother, more uniform texture.

In patients with photodamaged, wrinkled, blotchy facial skin, the treatment according to this invention likewise provided a significant improvement in appearance, even better than typically achieved with a-hydroxy acid and trichloroacetic acid chemical peels. The benefits included bleaching or lightening of hyperpigmented areas, such as age or liver spots; formation of smooth, unblemished skin having uniform texture and color; removal of comedones and horny masses in the follicles; and formation of a smoother, more supple, more elastic skim.

This treatment with the concentrated salicylic acid solution was repeated with some patients, as necessary or as desired, at two to four week intervals. With repeated applications, the same events occurred except that the treated skin tended to scale to a greater extent. Although a single treatment was usually efficacious, greater and more improved benefits were achieved with about 2 to 4 peels with the concentrated salicylic acid solution.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claim.

We claim:

1. A method for effecting a superficial chemical skin peel which comprises topically applying to skin to be treated a solution of salicylic acid containing at least 15 wt % up to a saturation concentration of salicylic acid, based on the weight of the solution, in a dermatologically acceptable, volatile, liquid solvent, allowing the salicylic acid to be present as a solution on a surface of the skin for a time sufficient to produce a chemical peel of stratum corneum of the skin with viable epidermis remaining substantially intact, allowing the applied solution to dry on the skin, and wiping the treated skin after the applied solution has dried, to remove residue from the applied solution from the skin.

2. The method of claim 1 wherein the salicylic acid is present in the solution in an amount of at least about 20 wt %.

3. The method of claim 1 wherein the salicylic acid is present in the solution in an amount of at least about 30 wt %.

4. The method of claim 1 wherein the solvent is selected from the group consisting of ethanol, isopropanol, methanol, acetone and diethyl ether.

5. The method of claim 1 wherein the solution comprises salicylic acid in ethanol.

6. The method of claim 1 wherein the treated skin is wiped with water.

7. The method of claim 1 wherein the step of wiping the treated skin occurs no later than one hour after the solution has been applied, to remove residual applied solution.

8. The method of claim 7 wherein the treated skin is wiped with water.

9. The method of claim 1 wherein the treated skin is facial skin.

10. The method of claim 1 wherein the skin being treated is affected with a skin disorder selected from the group consisting of photodamaged skin, hyperpigmentation, acne vulgaris, rosacea, premalignant skin cancer, wrinkles and superficial scarring.

11. The method of claim 10 wherein the skin disorder is hyperpigmentation.

12. The method of claim 10 wherein the skin disorder is acne vulgaris, selected from inflammatory acne, comedonal acne and acne-induced scarring.

* * * * *